United States Patent
Sun et al.

(10) Patent No.: US 9,301,967 B2
(45) Date of Patent: Apr. 5, 2016

(54) METHOD FOR PREPARING PHARMACEUTICAL COMPOSITION FOR ENHANCING IMMUNITY AND PHARMACEUTICAL COMPOSITION PREPARED ACCORDING TO THE METHOD

(75) Inventors: Dejun Sun, Changchun (CN); Jinlong Yin, Changchun (CN); Miaonan Sun, Changchun (CN); Yizhuo Zhao, Changchun (CN); Chunsheng Guo, Changchun (CN); Yanhui Gao, Changchun (CN); Xue Li, Changchun (CN)

(73) Assignee: Jilin Zixin Pharmaceutical Research Institution LLC., Changchun, Jilin (CN)

( * ) Notice: Subject to any disclaimer, the term of this patent is extended or adjusted under 35 U.S.C. 154(b) by 352 days.

(21) Appl. No.: 13/980,008

(22) PCT Filed: Jul. 14, 2011

(86) PCT No.: PCT/CN2011/077171
§ 371 (c)(1),
(2), (4) Date: Jul. 16, 2013

(87) PCT Pub. No.: WO2012/097575
PCT Pub. Date: Jul. 26, 2012

(65) Prior Publication Data
US 2013/0302379 A1 Nov. 14, 2013

(30) Foreign Application Priority Data

Jan. 21, 2011 (CN) .......................... 2011 1 0023849

(51) Int. Cl.
| | |
|---|---|
| A61K 36/00 | (2006.01) |
| A61K 36/25 | (2006.01) |
| A61K 31/7028 | (2006.01) |
| A61K 36/258 | (2006.01) |
| A23L 1/30 | (2006.01) |
| A61K 36/18 | (2006.01) |
| C12P 39/00 | (2006.01) |
| C12P 1/04 | (2006.01) |

(52) U.S. Cl.
CPC ........... *A61K 31/7028* (2013.01); *A23L 1/3002* (2013.01); *A61K 36/18* (2013.01); *A61K 36/258* (2013.01); *C12P 1/04* (2013.01); *C12P 39/00* (2013.01); *A61K 2236/00* (2013.01)

(58) Field of Classification Search
None
See application file for complete search history.

*Primary Examiner* — Qiuwen Mi

(57) ABSTRACT

A method for preparing a pharmaceutical composition for enhancing immunity and a pharmaceutical composition prepared according to the method. The method includes steps of: mixing ginseng ethanol extract with fruit and vegetable fermentation conversion solution to obtain a mixture, namely, the pharmaceutical composition for enhancing immunity; wherein the ginseng ethanol extract is prepared by a following step of: reflux extracting ginseng by ethanol aqueous solution for obtaining the extract, namely, the ginseng ethanol extract; the fruit and vegetable fermentation conversion solution is prepared by following steps of: mixing fruit and vegetable, *lactobacillus acidophilus* bacteria solution, *bifidobactreium longum* bacteria solution, *lactobacillus delbrueckii* subsp. *bulgaricus* bacteria solution, *streptococcus thermophilus* bacteria solution with water, and then fermenting for obtaining a fermentation product, namely, the fruit and vegetable fermentation conversion solution.

20 Claims, No Drawings

METHOD FOR PREPARING PHARMACEUTICAL COMPOSITION FOR ENHANCING IMMUNITY AND PHARMACEUTICAL COMPOSITION PREPARED ACCORDING TO THE METHOD

BACKGROUND OF THE PRESENT INVENTION

1. Field of Invention

The present invention relates to a pharmaceutical composition prepared for enhancing immunity and a method for preparing the pharmaceutical composition.

2. Description of Related Arts

Immunity is the body's own defense mechanism, and is the ability that the human body identifies and eliminates any invasive alien foreign bodies (such as viruses and bacteria); deals with aging, damaged, dead, degenerate own cells; and identifies and deals with mutant cells and virus-infected cells in the human body. Modern immunology thinks immunity is the physiological response that the human body identifies and eliminates "dissidents". In the human body, the immune system performs the above mentioned function. In the millions of years, the human lives in an environment both adapted for living and full of dangers, survives and obtains the extraordinary immunity. Therefore, it can be said that immunity is the product of the process of biological evolution.

Ginseng: the root of araliaceae plant ginseng. More than 30 kinds of total saponins of *panax ginseng* and pseudoginsenoside saponin F11 and polysaccharide can be separated from ginseng. Saponin is the material base of the physiological activity of ginseng.

Fruit and vegetable ferment (fermentation conversion solution): fruit and vegetable transformation stock solution is the all functional natural food which is extracted from more than 60 kinds of natural vegetable and fruit plant essences, and then is implanted with beneficial bacteria for fermenting and maturing, it is rich in complete vitamins, minerals, and amino acids, and is capable of providing the cells with the complete nutrients, repairing cells, and increasing the (biochemical reaction) efficiency of the cellular response to other beneficial ingredients.

Fruit and vegetable ferment (fermentation conversion solution) has the following physiological effects of:

(1) adjusting the environment in the human body, purifying the blood, improving the physical fitness, decomposing and excluding foreign bodies, preventing chronic and degenerative diseases;

(2) improving the capacity to transport of the leukocytes, promoting the function of the leukocytes, improving the anti-inflammatory, anti-bacterial and self-healing ability of the organisms;

(3) multi-factors involved in the decomposition and digestion of the food for making the food more digestible and absorbed to promote the physical recovery;

(4) promoting cell metabolism, generating energy, promoting the regeneration of the sub-healthy cells;

(5) resurrecting the recessionary germ cells, enhancing reproductive function;

(6) dispelling the effects of alcohol, anti-intoxicating; and (7) supplementing nutrition and energy sources.

SUMMARY OF THE PRESENT INVENTION

An object of the present invention is to provide a ginseng ferment composition for enhancing immunity and a method for preparing the ginseng ferment composition.

The method provided by the present invention comprises steps of:

mixing ginseng ethanol extract containing total saponins of *panax ginseng* with fruit and vegetable fermentation conversion solution to obtain a mixture, namely, a pharmaceutical composition for enhancing immunity;

wherein the ginseng ethanol extract containing total saponins of *panax ginseng* is prepared by the following step of: reflux extracting ginseng by ethanol aqueous solution for obtaining the extract, namely, the ginseng ethanol extract containing total saponins of *panax ginseng*;

wherein the fruit and vegetable fermentation conversion solution is prepared by the following steps of: mixing fruit and vegetable, *lactobacillus acidophilus* bacteria solution, *bifidobactreium longum* bacteria solution, *lactobacillus delbrueckii* subsp. *bulgaricus* bacteria solution, *streptococcus thermophilus* bacteria solution with water, and fermenting for obtaining the fermentation product, namely, the fruit and vegetable fermentation conversion solution.

In the method, every 1 L mixture is prepared by the following steps of: mixing the ginseng ethanol extract containing total saponins of *panax ginseng* with the fruit and vegetable fermentation conversion solution, and complementing a volume by the fruit and vegetable fermentation conversion solution for making a concentration of the total saponins of *panax ginseng* in the mixture 1.5 g/l-50 g/l;

every 1 L mixture is prepared by the following steps of: mixing the ginseng ethanol extract containing total saponins of *panax ginseng* with the fruit and vegetable fermentation conversion solution, and complementing a volume by the fruit and vegetable fermentation conversion solution for making a concentration of the total saponins of *panax ginseng* in the mixture 1.5 g/l, 15 g/l or 50 g/l.

In the method for preparing the ginseng ethanol extract containing total saponins of *panax ginseng*:

a time of every reflux extraction is 2 h-5 h, and especially, the time of every reflux extraction is 2 h, 3 h or 5 h;

a concentration of the ethanol aqueous solution is 70% (by volume);

in the method for preparing the fruit and vegetable fermentation conversion solution:

a temperature of the fermentation is 18° C.-37° C., and especially, the temperature of the fermentation is 18° C., 23° C. or 37° C., a time of the fermentation is 10 days-180 days, and especially, the time of the fermentation is 10 days, 15 days or 180 days, and a mode of the fermentation is fermentation with stirring.

The method for preparing the ginseng ethanol extract containing total saponins of *panax ginseng* further comprises following steps of:

removing ethanol from the extract, and then concentrating and drying, thereby obtaining a dried product, namely, the ginseng ethanol extract containing total saponins of *panax ginseng*;

The method for preparing the fruit and vegetable fermentation conversion solution, before fermenting, further comprises a step of grinding the fruit and vegetable with a size of 40-50 meshes;

after fermenting, further comprises steps of: filtering the fermentation product, collecting the filtrate, ultra-filtering, and collecting the ultra-filtered liquid, namely, the fruit and vegetable fermentation conversion solution.

The ultra-filtering is ultra-filtering the filtrate by 100,000 molecular weight (with a liquid inlet pressure of 1.3 kg, and a liquid outlet pressure of 0.5 kg).

The fruit and vegetable is a mixture containing 54 kinds of fruits and vegetables as below:

konjak, eggplant, asparagus, spinach, bean sprouts, cauliflower, cabbage, radish, cucumber, pea, cayenne pepper, celery, onion, garlic, grape, grapefruit, watermelon, peach, tangerine, blueberry, sweet orange, banana, litchi, bitter gourd, Chinese chive, pomegranate, pitaya, carrot, tomato, Chinese cabbage, western celery, sweet pepper, lettuce, pear, ginger, taro, kidney bean, pumpkin, lotus root, cherry, kiwi, smoked plum, strawberry, fig, kumquat, poon kan, southland pear, muskmelon, melon, papaya, onion, mulberry, sugar beet and lemon.

In the fruit and vegetable, every fruit and vegetable has the same weight.

In the method for preparing the ginseng ethanol extract containing total saponins of *panax ginseng*:

a ratio of the ethanol aqueous solution to the ginseng is (1-10) ml:1g;

and especially, the ratio of the ethanol aqueous solution to the ginseng is (1, 5, or 10) ml:1g;

In the method for preparing the fruit and vegetable fermentation conversion solution:

a ratio of the *lactobacillus acidophilus* bacteria solution, the *bifidobactreium longum* bacteria solution, the *lactobacillus delbrueckii* subsp. *bulgaricus* bacteria solution, the *streptococcus thermophilus* bacteria solution, the fruit and vegetable and water is (2000-8000) ml:(2000-8000) ml:(2000-8000) ml:(2000-8000) ml:(1000-1500) kg:(1000-1500) kg;

the ratio of the *lactobacillus acidophilus* bacteria solution, the *bifidobactreium longum* bacteria solution, the *lactobacillus delbrueckii* subsp. *bulgaricus* bacteria solution, the *streptococcus thermophilus* bacteria solution, the fruit and vegetable and water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg;

the *lactobacillus acidophilus* bacteria solution is prepared by a following step of: fermental culturing *lactobacillus acidophilus* for obtaining a fermentation product, namely, the *lactobacillus acidophilus* bacteria solution; a fermentation temperature is 20° C.-41° C., and especially, the fermentation temperature is 20° C., 37° C., or 41° C., a fermentation time is 15 h-36 h, and especially, the fermentation time is 15 h, 16 h or 36 h;

the *bifidobactreium longum* bacteria solution is prepared by a following step of: fermental culturing *bifidobactreium longum* for obtaining a fermentation product, namely, the *bifidobactreium longum* bacteria solution; a fermentation temperature is 20° C.-41° C., and especially, the fermentation temperature is 20° C., 37° C., or 41° C., a fermentation time is 15 h-36 h, and especially, the fermentation time is 15 h, 16 h or 36 h;

the *lactobacillus delbrueckii* subsp. *bulgaricus* bacteria solution is prepared by a following step of: fermental culturing *lactobacillus delbrueckii* subsp. *bulgaricus* for obtaining a fermentation product, namely, the *lactobacillus delbrueckii* subsp. *bulgaricus* bacteria solution; a fermentation temperature is 20° C.-41° C., and especially, the fermentation temperature is 20° C., 37° C., or 41° C., a fermentation time is 15 h-36 h, and especially, the fermentation time is 15 h, 16 h or 36 h;

the *streptococcus thermophilus* bacteria solution is prepared by a following step of: fermental culturing *streptococcus thermophilus* for obtaining a fermentation product, namely, the *streptococcus thermophilus* bacteria solution; a fermentation temperature is 20° C.-41° C., and especially, the fermentation temperature is 20° C., 37° C., or 41° C., a fermentation time is 15 h-36 h, and especially, the fermentation time is 15 h, 16 h or 36 h.

The *lactobacillus acidophilus* is *lactobacillus acidophilus* CGMCC 1.1854, the *bifidobactreium longum* is *bifidobactreium longum* CGMCC 1.2186, the *lactobacillus delbrueckii* subsp. *bulgaricus* is *lactobacillus delbrueckii* subsp. *bulgaricus* CGMCC 1.1480, the *streptococcus thermophilus* is *streptococcus thermophilus* CGMCC 1.2471.

The formula of every fermentally cultured medium is as below: 10 g peptone, 10 g beef extract, 5 g yeast extract, 20 g glucose, 1 g Tween-80, 2 g $K_2HPO_4$, 1 g Tween-80, 5 g NaAC, 2 g ammonium citrate, 0.2 g $MgSO_4$, 0.05 g $MnSO_4$ are mixed with water, and then supplemented with water to make the volume equal to 1 L for obtaining the medium.

The pharmaceutical composition for enhancing immunity prepared by the above-mentioned method is also the scope of protection of the present invention.

Experiments of the present invention show that the ginseng ethanol extract and fruit and vegetable fermentation conversion solution extracted by the method of the present invention have short extraction time and large extraction amount, the ginseng ethanol extract and fruit and vegetable fermentation conversion solution are used as the main materials to prepare the pharmaceutical composition for enhancing immunity. Moreover, according to Chinese immunocompromised people with large proportion of sub-health and accompanied by high blood sugar symptoms, the flavoring agent of the present product adopts the yum sugar for reducing the usage amount of sweetener, such as glucose and sucrose, easily leading to hyperglycemia in the oral liquid to benefit more people.

DETAILED DESCRIPTION OF THE PREFERRED EMBODIMENT

If no special instructions, the experimental methods used in the following embodiments are conventional methods.

If no special instructions, the materials, the reagents and so on in the following embodiments can be commercially obtained.

Embodiment 1

Obtain the Ginseng Ferment Composition for Enhancing Immunity

Method 1:

1. Prepare the Ginseng Ethanol Extract (1) Prepare raw materials: ginseng (purchased from Jilin Zixin Pharmaceutical Co., Ltd) is in accordance with the regulation of "Pharmacopoeia of the People's Republic of China". The quality is monitored strictly in accordance with the enterprise standard requirements before feeding.

(2) Weigh the ginseng according to the formula ratio, and then wash, drain, reflux extract twice by 70% ethanol aqueous solution with ten times (v/w) of the amount, every extract time is 3 h; filter, merge the filtrate, and depressurizedly recover the ethanol.

(3) When the filtrate is concentrated to be with the relative density of 1.10-1.15 (0.07 MPa, 70° C.), spray-dry (wherein the inlet temperature is 170° C., the outlet temperature is 70° C.) for obtaining the spray-dried fine powder, namely, the ginseng ethanol extract containing total saponins of *panax ginseng*.

(4) Warehousing after test qualification according to enterprise standards.

The test method of total saponins of *panax ginseng* is colorimetric assay, which is specifically described as follows:

(4.1) Reagents and Instruments:

Amberlite-XAD-2 macroporous resin, America Sigma chemical company; n-butanol, ethanol, analytical pure; neutral alumina for chromatography with the size of 100-200 meshes; ginsenoside Re purchased from Chinese Drug and Biological Product Verification Institute; vanillin solution, weigh 5 g vanillin solution added with glacial acetic acid for dissolving and determining the volume to 100 ml; perchloric acid, glacial acetic acid, analytical pure; ginsenoside Re standard solution, accurately weigh 0.020 g ginsenoside Re standard solution, and then dissolve by methanol and determine the volume to 10.0 ml, namely, every 1 ml contains ginsenoside Re 2.0 mg; colorimeter, UV-4802H type, product by Unocal Company; Chromatography tube, 10 ml syringe.

(4.2) Experimental Procedure (4.2.1) Sample Treatment

Weigh about 1.0 g sample, place the sample into a volumetric flask with the volume of 100 ml, add a little water, ultrasound for 30 min, determine the volume by water to 100 ml, shake evenly, place for 15 min, absorb 1.0 ml supernatant for column chromatography.

(4.2.2) Column Chromatography

Use 10 ml syringe as the chromatography tube, place 1 g Amberlite-XAD-2 macroporous resin in the syringe, add neutral alumina with the height of 1 cm on the macroporous resin. Firstly, the column is washed with 25 ml 70% ethanol, and then washed with 25 ml water, the eluent is abandoned, 1.0 ml treated sample solution is accurately added, the column is washed with 25 ml water for washing away the sugar and other water-soluble impurities, and then the total saponins of *panax ginseng* is eluted with 25 ml 70% ethanol, the eluent is collected in the evaporating dish and dried at 60° C. water bath, which is used for coloring.

(4.2.3) Coloring

Accurately add 0.2 ml 5% vanillin glacial acetic acid solution into the above-mentioned dried evaporating dish, turn the evaporating dish for dissolving the residue, and then add 0.8 ml perchloric acid to evenly mix, and then move to 5 ml graduated centrifuge tube with stopper, heat at 60° C. water bath for 10 min, remove, cool at ice bath, and then accurately add 5.0 ml glacial acetic acid, shake evenly, colorimetrically determine with the standard tube at the wavelength of 560 nm by 1 cm colorimetric cell.

(4.2.4) Calibration Curve

Absorb 100 μL ginsenosides Re standard solution (2.0 mg/ml) to put in the evaporating dish, dry at water bath (lower than 60° C.), or dry by heat air (do not allow overheating), which is the same as the sample. Measure the absorbance value.

(5) Calculate:

In the formula:

$$X = (A_1 \times C \times V \times 100 \times 1)/A_2 \times m \times 1000 \times 1000$$

X—the total saponins of *panax ginseng* in the sample, g/100 g;

$A_1$—the absorbance value of the standard solution;

$A_2$—the absorbance value of the standard solution;

C—the amount of the total saponins of *panax ginseng* in the standard tube, μg

V—the dilution volume of the sample, ml;

m—the quality of the sample, g;

The calculation result remains two significant digits. The result is that the content of the total saponins of *panax ginseng* is 30 g in 100 g sample.

2. Prepare the Fruit and Vegetable Fermentation Conversion Solution (1) Select the following 54 kinds of fruit and vegetable materials

TABLE 1

54 kinds of fruit and vegetable materials

| Materials | Nutritional components |
| --- | --- |
| Konjak | Vitamins B1 and B2, citric acid, fruit and vegetable fermentation conversion matter |
| Eggplant | Vitamins A, B1, B2 and C, fruit and vegetable fermentation conversion matter |
| Asparagus | Vitamins B1 and B2, citric acid, fruit and vegetable fermentation conversion matter |
| Spinach | Vitamins A and C, iron, calcium, fruit and vegetable fermentation conversion matter |
| Bean sprouts | Vitamin, fragrant soap, amino acid, fruit and vegetable fermentation conversion matter |
| Cauliflower | Vitamins B1 and B2, citric acid, fruit and vegetable fermentation conversion matter |
| Cabbage | Vitamins B1 and B2, citric acid, fruit and vegetable fermentation conversion matter |
| Radish | Vitamins B1 and B2, citric acid, fruit and vegetable fermentation conversion matter |
| Cucumber | Vitamins B1 and B2, citric acid, fruit and vegetable fermentation conversion matter |
| Pea | Vitamins B1 and B2, citric acid, fruit and vegetable fermentation conversion matter |
| Cayenne pepper | Vitamins B1 and B2, citric acid, fruit and vegetable fermentation conversion matter |
| Celery | Vitamins B1 and B2, citric acid, fruit and vegetable fermentation conversion matter |
| Onion | Vitamins B1 and B2, citric acid, fruit and vegetable fermentation conversion matter |
| Garlic | Vitamins B1 and B2, citric acid, fruit and vegetable fermentation conversion matter |
| Grape | Vitamins B1 and B2, citric acid, fruit and vegetable fermentation conversion matter |
| Grapefruit | Vitamins B1 and B2, citric acid, fruit and vegetable fermentation conversion matter |
| Watermelon | Vitamins B1 and B2, citric acid, fruit and vegetable fermentation conversion matter |
| Peach | Vitamins B1 and B2, citric acid, fruit and vegetable fermentation conversion matter |
| Tangerine | Vitamins Bl, B2 and C, fruit and vegetable fermentation conversion matter |
| Blueberry | Vitamins B1 and B2, citric acid, fruit and vegetable fermentation conversion matter |
| Sweet orange | Vitamins B1 and B2, citric acid, fruit and vegetable fermentation conversion matter |
| Banana | Vitamins B1 and B2, citric acid, fruit and vegetable fermentation conversion matter |
| Litchi | Vitamins B1 and B2, citric acid, fruit and vegetable fermentation conversion matter |
| Bitter gourd | Vitamins B1 and B2, citric acid, fruit and vegetable fermentation conversion matter |
| Chinese chive | Vitamins B1 and B2, citric acid, fruit and vegetable fermentation conversion matter |
| Pomegranate | Vitamins B1 and B2, citric acid, fruit and vegetable fermentation conversion matter |
| Pitaya | Vitamins B1 and B2, citric acid, fruit and vegetable fermentation conversion matter |
| Carrot | Vitamin A, carotene, fruit and vegetable fermentation conversion matter |
| Tomato | Vitamin A, carotene, citric acid, fruit and vegetable fermentation conversion matter |
| Chinese cabbage | Vitamin, mineral, fruit and vegetable fermentation conversion matter |
| Western celery | Vitamin, mineral, cellulose, fruit and vegetable fermentation conversion matter |
| Sweet pepper | Vitamin C, mineral, fruit and vegetable conversion matter |
| Lettuce | Vitamin A, mineral, fruit and vegetable fermentation conversion matter |

TABLE 1-continued 54 kinds of fruit and vegetable materials

| Materials | Nutritional components |
|---|---|
| Pear | Fructose, mineral, fruit and vegetable fermentation conversion matter |
| Ginger | Vitamin, mineral, fruit and vegetable fermentation conversion matter |
| Taro | Vitamins B1, B2 and C, mineral, fruit and vegetable fermentation conversion matter |
| Kidney bean | Vitamins B1 and B2, citric acid, fruit and vegetable fermentation conversion matter |
| Pumpkin | Carotene, mineral, fruit and vegetable fermentation conversion matter |
| Lotus root | Iron, tannin, fruit and vegetable fermentation conversion matter |
| Cherry | Mineral, fruit and vegetable fermentation conversion matter |
| Kiwi | Vitamin C, fruit and vegetable fermentation conversion matter |
| Smoked plum | Organic acid, vitamin, fruit and vegetable fermentation conversion matter |
| Strawberry | Vitamin C, mineral, ellagic acid, fruit and vegetable fermentation conversion matter |
| Fig | Digestion fruit and vegetable fermentation conversion matter, vitamin, mineral |
| Kumquat | Vitamins B1, B2 and C, fruit and vegetable fermentation matter |
| Poon kan | Vitamin C, citric acid, fruit and vegetable fermentation conversion matter |
| Southland pear | Vitamins Bl, B2, C, citric acid, fruit and vegetable fermentation conversion matter |
| Muskmelon | Vitamins B1 and B2, citric acid, fruit and vegetable fermentation conversion matter |
| Melon | Fructose, potassium, vitamin A, fruit and vegetable fermentation conversion matter |
| Papaya | Vitamins B, C and E, citric acid, carotene, fruit and vegetable fermentation conversion matter |
| Onion | Vitamins B and C, carotene, fruit and vegetable fermentation conversion matter |
| Mulberry | Vitamins B1 and B2, citric acid, fruit and vegetable fermentation conversion matter |
| Sugar beet | Betaine, fruit and vegetable fermentation conversion matter |
| Lemon | Citric acid, fruit and vegetable fermentation conversion matter |

(2) Fermentable Conversion of the Fruit and Vegetable

1) The Selection and Purchase of the Strain

Probiotics are purchased from Institute of Microbiology, Chinese Academy of Sciences, the probiotics are respectively *lactobacillus acidophilus* CGMCC 1.1854, *bifidobactreium longum* CGMCC 1.2186, *lactobacillus delbrueckii* subsp. *bulgaricus* CGMCC 1.1480, *streptococcus thermophilus* CGMCC 1.2471, all stain tailings soil pipes preserve the stains as the original strains.

2) Prepare the Master Seed

Prepare the probiotics master seed (the passage of the master seed is less than or equal to 10 generations, the passage of the present preparation method is 4 generations)

① By a sterile stainless steel spoon, respectively take *lactobacillus acidophilus* CGMCC 1.1854, *bifidobactreium longum* CGMCC 1.2186, *lactobacillus delbrueckii* subsp. *bulgaricus* CGMCC 1.1480, *streptococcus thermophilus* CGMCC 1.2471 for 1/10 amount of the sand tube, the rest being frozen, in the 50 ml (250 conical flask) MRS liquid medium (10 g/l peptone, 10 g/l beef extract, 5 g/l yeast extract, 20 g/l glucose, 1 g/l Tween-80, 2 g/l $K_2HPO_4$, 1 g/l Tween-80, 5 g/l NaAC, 2 g/l ammonium citrate, 0.2 g/l $MgSO_4$, 0.05 g/l $MnSO_4$, sterilized at 121° C. for 20 min), shaking culture with 100 revolutions at 37° C. for 16 h;

② Respectively select one ring and streak inoculate on MRS solid culture medium (10 g/l peptone, 10 g/l beef extract, 5 g/l yeast extract, 20 g/l glucose, 1 g/l Tween-80, 2 g/l $K_2HPO_4$, 1 g/l Tween-80, 5 g/l NaAC, 2 g/l ammonium citrate, 0.2 g/l $MgSO_4$, 0.05 g/l $MnSO_4$, 1.5% agar, sterilized at 121° C. for 20 min), culture by an incubator at 37° C. for 16 h;

③ Respectively select a colony with the most prosperous growing to connected to a 50 ml MRS liquid culture medium, shaking culture with 180 revolutions at 30° C. for 16 h;

④ Respectively connect to a 500 ml MRS liquid culture medium, shaking culture with 100 revolutions at 37° C. for 16 h, add glycerol till 20%, shake uniformly, separately put to a cryogenic vial with the volume of 1 ml for being regarded as the master seed of probiotic *lactobacillus acidophilus, bifidobactreium longum, bifidobactreium breve*, and *streptococcus thermophilus* which is preserved below the temperature of −40° C.;

(3) Prepare the Working Seed

Prepare the probiotics working seed (the passage of the working seed is less than or equal to 5 generations, the passage of the present preparation method is 4 generations)

① By a sterile inoculating loop, respectively take *lactobacillus acidophilus* CGMCC 1.1854, *bifidobactreium longum* CGMCC 1.2186, *lactobacillus delbrueckii* subsp. *bulgaricus* CGMCC 1.1480, *streptococcus thermophilus* CGMCC 1.2471 master seeds, respectively streak inoculate on a MRS solid culture medium, culture by an incubator at 37° C. for 16 h;

② Respectively select a colony with the most prosperous growing to be connected to a 50 ml MRS liquid culture medium, shaking culture with 100 revolutions at 37° C. for 16 h;

③ Respectively connect to a 500 ml MRS liquid culture medium, shaking culture with 100 revolutions at 37° C. for 16 h;

④ Respectively connected to a 5000 ml MRS liquid culture medium again, stir with 100 revolutions at 37° C., culture for 16 h; thereby obtaining *lactobacillus acidophilus* CGMCC 1.1854 bacteria solution, *bifidobactreium longum* CGMCC 1.2186 bacteria solution, *lactobacillus delbrueckii* subsp. *bulgaricus* CGMCC 1.1480 bacteria solution, *streptococcus thermophilus* CGMCC 1.2471 bacteria solution. The above-mentioned bacteria solutions are all fermentation products in the fermentation vessel.

(4) Deal with the Fruit and Vegetable

1) Weigh the above-mentioned materials;
2) Wash and remove impurities, dry the moisture, weigh;
3) grind to be 40-50 meshes, and put into the fermentor;

For 3 tons fermentor (effective using solvent=3 tons× 0.8=2.4 tons), the actual feeding is controlled to 2400 kg; according to the proportion of the fruit and vegetable 1:1, the feeding of the fruit and vegetable is 1200 kg, the added water is 1200 kg.

(5) The Fermentable Conversion of the Fruit and Vegetable Quick Hydrolysate

Respectively add 5000 ml *lactobacillus acidophilus* CGMCC 1.1854 bacteria solution, *bifidobactreium longum* CGMCC 1.2186 bacteria solution, *lactobacillus delbrueckii* subsp. *bulgaricus* CGMCC 1.1480 bacteria solution, *streptococcus thermophilus* CGMCC 1.2471 bacteria solution to the fermenter again, wherein the fermentation temperature is controlled to 23° C., stir for 15 d;

3) Filter by the filter cloth with 200 meshes, discard the residues of the fruit and vegetable, and take the filtrate;

4) The filtrate is ultra filtered via 100,000 molecular weight (with the liquid inlet pressure of 1.3 kg and the liquid outlet pressure of 0.5 kg) for obtaining 1200-1500 kg clear liquid, and then sealed, preserved at 4° C., thereby obtaining the fruit and vegetable fermentation conversion solution.

(6) Test

The main products of the fruit and vegetable fermentation conversion solution are lactate and acetic acid. Therefore, the acidity is regarded as the characteristic component for identifying, which is presented as follows:

The acidity of the fruit and vegetable fermentation conversion solution: the milliliters of the consumed 0.1N NaOH solution while dropping 100 ml fruit and vegetable fermentation conversion solution. While testing, 10 ml sample is generally used.

Measurement steps: take 10 ml fruit and vegetable fermentation conversion solution+20 ml water+0.5 ml 0.5% phenolphthalein indicator, use 0.1N NaOH standard solution to titrate till the color is reddish for 30 seconds without fading. Calculate: acidity=the volume of the consumed 0.1N NaOH standard solution×10

Result: the acidity of this product is 42.

3. Prepare the Composite

Mix the above obtained ginseng ethanol extract with the fruit and vegetable fermentation conversion solution according to the following formula:

Mix the ginseng ethanol extract containing total saponins of *panax ginseng* with the fruit and vegetable fermentation conversion solution, use the fruit and vegetable fermentation conversion solution to supplement till the volume is 1 L, thereby obtaining the composite, the concentration of total saponins of *panax ginseng* in the composite is 15 g/l.

Method 2:

1. Prepare the Ginseng Ethanol Extract

The extraction method and the first method are substantially identical, and the difference is that ginseng is reflux extracted by double the amount (v/w) of 70% ethanol aqueous for 3 h;

The detection method and the first method are identical, and the result is that 100 g ginseng ethanol extract contains 40 g total saponins of *panax ginseng*.

2. Prepare the Fruit and Vegetable Fermentation Conversion Solution

The extraction method and the first method are substantially identical, and the difference is that respectively add 2000 ml *lactobacillus acidophilus* CGMCC 1.1854 bacteria solution, *bifidobactreium longum* CGMCC 1.2186 bacteria solution, *lactobacillus delbrueckii* subsp. *bulgaricus* CGMCC 1.1480 bacteria solution, *streptococcus thermophilus* CGMCC 1.2471 bacteria solution, 1000 kg fruit and vegetable and 1000 kg water.

The fermentation temperature of the fruit and vegetable fermentation conversion solution is 18° C., and the fermentation time thereof is 10 days.

The fermentation temperature of the *lactobacillus acidophilus* bacteria solution, the *bifidobactreium longum* bacteria solution, the *lactobacillus delbrueckii* subsp. *bulgaricus* bacteria solution, and the *streptococcus thermophilus* bacteria solution is 20° C., and the fermentation time thereof is 15 h.

The detection method and the first method are identical, and the result has no significant difference with the first method.

3. Prepare the Composition

The preparation of the composition of the second method and that of the first method are identical, and the difference is that the ginseng ethanol extract containing total saponins of *panax ginseng* obtained by the second method is mixed with the fruit and vegetable fermentation conversion solution, and the fruit and vegetable fermentation conversion solution is complemented till the volume is 1 L for obtaining the composition, the content of total saponins of *panax ginseng* in the composition is 1.5 g/l.

Method 3:

1. Prepare the Ginseng Ethanol Extract

The extraction method and the first method are substantially identical, and the difference is that ginseng is reflux extracted by five times the amount (v/w) of 70% ethanol aqueous for 5 h;

The detection method and the first method are identical, and the result is that 100 g ginseng ethanol extract contains 50 g total saponins of *panax ginseng*.

2. Prepare the Fruit and Vegetable Fermentation Conversion Solution

The extraction method and the first method are substantially identical, and the difference is that respectively add 8000 ml *lactobacillus acidophilus* CGMCC 1.1854 bacteria solution, *bifidobactreium longum* CGMCC 1.2186 bacteria solution, *lactobacillus delbrueckii* subsp. *bulgaricus* CGMCC 1.1480 bacteria solution, *streptococcus thermophilus* CGMCC 1.2471 bacteria solution, 1500 kg fruit and vegetable and 1500 kg water.

The fermentation temperature of the fruit and vegetable fermentation conversion solution is 37° C., and the fermentation time thereof is 180 days.

The fermentation temperature of the *lactobacillus acidophilus* bacteria solution, the *bifidobactreium longum* bacteria solution, the *lactobacillus delbrueckii* subsp. *bulgaricus* bacteria solution, and the *streptococcus thermophilus* bacteria solution is 41° C., and the fermentation time thereof is 36 h.

The detection method and the first method are identical, and the result has no significant difference with the first method.

3. Prepare the Composition

The preparation of the composition of the third method and that of the first method are identical, and the difference is that the ginseng ethanol extract containing total saponins of *panax ginseng* obtained by the third method is mixed with the fruit and vegetable fermentation conversion solution, and the fruit and vegetable fermentation conversion solution is complemented till the volume is 1 L for obtaining the composition, the content of total saponins of *panax ginseng* in the composition is 50 g/l.

Embodiment 2

Prepare Ginseng Enzyme Oral Liquid

Production condition: Air cleanliness of the production environment is 100,000 grades Specific Production Method:

1. The composition obtained by the first method of the first embodiment is mixed with the flavoring (specifically white sugar purchased from Changchun Ouya Market) (10%, w/v), and then is put to the mixing liquid tank to mix for 30 min to ensure the uniformity, and then is instantaneously sterilized at high heat, thereby obtaining the ginseng enzyme oral liquid.

2. Fill the oral liquid bottles: Use the oral liquid filling machine to fill the oral liquid bottles, every bottle is filled with 10 ml. During filling, it should be noted to monitor the differences between product qualities, which are controlled in the difference range.

3. Cap: The oral liquid bottles are capped by the oral liquid capper, and the nonconforming products are filtered.

4. Leak detection: The capper oral liquid is leak-detected by the vacuum leak detector.

5. Inner packing: The cardboard boxes are used and every cardboard box contains 10 bottles.

6. Outer packing: corrugated boxes are used.

7. Test: Test is in accordance with the corporate standards.

8. Warehousing: The products are not warehoused until the product inspection is qualified.

Embodiment 3

The Experimental Research on the Enhancing Immunity Function of the Ginseng Enzyme Oral Liquid 1. Materials and Methods 1.1 Test Substances The ginseng enzyme oral liquid obtained by the second embodiment is brown, and its mass density is 1.05. Every dose concentration is prepared by distilled water.

1.2 Experimental Animals 200 healthy Kunming female mice are provided by the experimental animal center of Jilin University, each of which has the body weight of 18-22 kg. Feeds and beddings also come from the above-mentioned place.

1.3 Animal Room Environment

The temperature is 20° C.-22° C., and the humidity is 45%-50%.

1.4 Dosage Choice 200 female mice are divided into 5 parts, 40 mice of every part are randomly divided into four groups, and every group consists of 10 mice. Every experimental dosage is designed to 20 ml/kg, 10.06 ml/kg and 5.0 ml/kg, one is solvent control group (which is provided with the equal volume distilled water by gavage, three are dose groups.

1.5 Experimental Methods

According to the dose, every group is treated by gavage once every day (the gavage capacity is 0.2 ml/10 g, the solvent control group is treated with equal volume distilled water by gavage) for 30 d, and then every immunity index of the animal is tested. The experimental methods are as follows.

1.5.1 Determination of the Delayed Type Hypersensitivity (DTH) in Mice:

At the $26^{th}$ day by gavage, 2% sheep erythrocyte with 0.2 ml every mouse (SRBC, Beijing Ding Guo Biotechnology Co., Ltd, v/v) is injected to the abdominal cavity of the mouse for sensitizing, at the $4^{th}$ day after immunity, 20% SRBC (20 μl every mouse) is subcutaneously injected to the left rear paw of every mouse for attacking. The thicknesses of the same position of the left rear foot intestine of every mouse are respectively measured at 24 h before attacking and 24 h after attacking, the difference therebetween is calculated, the result of every dose group is compared with that of the solvent control group for analysis of variance.

The result is shown in Table 2.

TABLE 2

DTH determination results of mice with ginseng enzyme oral liquid (24 h)

| Group ml/kg | The number of animals | The thickness difference of foot extension (mm) | P value |
|---|---|---|---|
| 10 | 10 | 0.947 ± 0.432 | 0.00 |
| 6.6 | 10 | 0.951 ± 0.414 | 0.00 |
| 3.3 | 10 | 0.743 ± 0.133 | 0.00 |
| Solvent control | 10 | 0.619 ± 0.071 | |

It can be seen from the above table, by SRBC attacking (with 24 h interval), the thickness difference of the mouse toe of every dose group is higher than that of the solvent control group, and the differences are statistically significant ($p<0.01$).

1.5.2 ConA Inducts Mouse Spleen Lymphocytes Transformation Experiments (MTT Method):

At the $26^{th}$ day by gavage, the spleen of the mouse of every group is sterilely taken, the spleen cell suspension is prepared, the spleen cell concentration is adjusted to $3\times10^{6}$/ml by RPMI 1640 complete culture medium (purchased from Beijing Ding Guo Biotechnology Co., Ltd). The lymphocyte proliferative responses are made according to the MTT method in the process, and finally, the absorbance value (A) at the wavelength of 570 nm is measured, the difference between the absorbance value of ConA$^+$ and that of ConA$^-$. The result of every dose group is compared with that of the solvent control group for analysis of variance.

The result is shown in Table 3

TABLE 3

Transformed measurement results of mice spleen lymphocytes with ginseng enzyme oral liquid

| Group ml/kg | The number of animals | The difference between ConA$^+$ and ConA$^-$ | P value |
|---|---|---|---|
| 10 | 10 | 0.161 ± 0.098 | 0.00 |
| 6.6 | 10 | 0.154 ± 0.086 | 0.00 |
| 3.3 | 10 | 0.125 ± 0.074 | 0.00 |
| Solvent control | 10 | 0.113 ± 0.039 | |

It can be seen from the above table that the difference between the absorbance value of ConA$^+$ and that of ConA$^-$ of every dose group is higher that that of the solvent control group, and the differences are statistically significant ($p<0.01$).

1.5.3 Determination of Serum Hemolysin

At the $25^{th}$ day by gavage, 20% SRBC (0.2 ml every mouse) is injected to the abdominal cavity of the mouse, at the $5^{th}$ day after immunity, the eyeball is picked for blood sampling, the serum is separated and the serum hemolysin is determined on the micro hemagglutination board: incubate at 37° C. for 3 h, the hemagglutination degree is counted, and the corresponding anti-volume number is calculated. The result of every dose group is compared with that of the solvent control group for analysis of variance.

The result is shown in Table 4, the anti-volume number of the mouse of every dose group is higher than that of the solvent control group, and the differences are statistically significant ($p<0.01$).

TABLE 4

Measurement results of mice serum hemolysin with ginseng enzyme oral liquid

| Group ml/kg | The number of animals | The number of anti-volume | P value |
|---|---|---|---|
| 10 | 10 | 182.23 ± 18.72 | 0.001 |
| 6.6 | 10 | 178.81 ± 16.87 | 0.004 |
| 3.3 | 10 | 181.75 ± 18.65 | 0.001 |
| Solvent control | 10 | 153.42 ± 8.79 | |

1.5.4 Detection on Antibody-Producing Cells (PFC)

At the $25^{th}$ day by gavage, 20% SRBC (0.2 ml every mouse) is injected to the abdominal cavity of the mouse, the mouse is sacrificed at the $5^{th}$ day after immunity, and then is dissected for picking the spleen to prepare the spleen cell suspension, the spleen cell concentration is adjusted to $5 \times 10^6$/ml by RPMI 1640 complete culture solution, the agarose glass is prepared according to the procedure method, and cultured in the $CO_2$ incubator (at 37° C., 5% $CO_2$) for 1.5 h and then added with the complement, and then cultured for 1.5 h, and the number of hemolytic plaque formed on every agarose glass is counted. The result of every dose group is compared with that of the solvent control group for analysis of variance.

The result can be seen from Table 5, the differences between the number of hemolytic plaque of the high dose group and that of the solvent control group are statistically significant (p<0.05), the differences between the number of hemolytic plaque of the medium and low dose groups and that of the solvent control group are not statistically significant (p>0.05).

TABLE 5

Measurement results of mice antibody-producing cells with ginseng enzyme oral liquid

| Group ml/kg | The number of animals | The number of hemolytic plaque/ $10^6$ spleen cells | P value |
|---|---|---|---|
| 10 | 10 | 911 ± 365 | 0.04 |
| 6.6 | 10 | 821 ± 187 | 0.095 |
| 3.3 | 10 | 815 ± 179 | 0.112 |
| Solvent control | 10 | 653 ± 151 | |

1.5.5 Carbon Clearance Experiment in Mice 0.1 ml/10 g india ink (diluted four time) is injected to the mouse tail vein of every group in accordance with the order. 20 μl blood is punctually inner canthus sampled by every mouse at 2 min and 10 min after being injected with the ink, and then quickly added to 2 ml 0.1% sodium carbonate solution and shaken evenly, the absorbance value (A) is measured at the wavelength of 600 nm by the UV-Vis spectrophotometer. Simultaneously, weigh the liver and spleen of the mouse and calculate the phagocytic index according to the formula. The result of every dose group is compared with that of the solvent control group for analysis of variance.

The results can be seen from Table 6, the differences between the mouse carbon clearance phagocytic index of the high dose group and that of the solvent control group are statistically significant (p<0.05), the differences between the mouse carbon clearance phagocytic index and the medium and low dose groups and that of the solvent control group are not statistically significant (p>0.05).

TABLE 6

Measurement results of mice carbon clearance experiment with ginseng enzyme oral liquid

| Group ml/kg | The number of animals | Phagocytic index | P value |
|---|---|---|---|
| 10 | 10 | 4.612 ± 0.381 | 0.028 |
| 6.6 | 10 | 3.981 ± 0.413 | 0.784 |
| 3.3 | 10 | 3.785 ± 0.397 | 0.995 |
| Solvent control | 10 | 3.746 | |

1.5.6 Experiments on Mouse Abdominal Macrophage Phagocytosis Chicken Erythrocytes:

After lastly given with the test substance, the abdominal cavity of every mouse of every group is injected with 1 ml 20% chicken erythrocyte suspension, the mouse is killed every 30 min, the abdominal cavity of every mouse is injected with 2 ml saline, shake for 1 min and then take the abdominal cavity lavage fluid for slice production, incubate at 37° C. for 30 min, rinse, fix and staining microscopy. Count the number of the macrophage phagocytosis chicken erythrocytes and the number of the chicken erythrocytes. The macrophage rate conversion value and the macrophage index of every dose group are compared with that of the solvent control group for analysis of variance.

The results can be seen from Table 7, the macrophage conversion value of the mouse macrophage phagocytosis chicken erythrocytes of every dose group is higher than that of the solvent control group, the differences between the high and medium dose groups and that of the solvent control group are statistically significant (p<0.05), the differences between the low dose group and that of the solvent control group are not statistically significant (p>0.05).

TABLE 7

Macrophage measurement results of mouse macrophage phagocytosis chicken erythrocytes with ginseng enzyme oral liquid

| Group ml/kg | The number of animals | The number of macrophages | Phagocytic rate conversion value | Phagocytic index |
|---|---|---|---|---|
| 10 | 10 | 100 × 10 | 65.71 ± 5.47 | 2.94 ± 1.15 |
| 6.6 | 10 | 100 × 10 | 64.27 ± 4.19 | 2.89 ± 1.04 |
| 3.3 | 10 | 100 × 10 | 62.84 ± 3.63 | 2.43 ± 0.96 |
| Solvent control | 10 | 100 × 10 | 50.39 ± 2.94 | 1.87 ± 1.09 |

It is proved by the animal experiments that: the measurement results of the oral liquid on the cellular immune function, the humoral immune function and the monocyte-macrophage function are positive. It is preliminarily proved that the oral liquid can enhance the immunity.

The same method is used to detect the compositions obtained by the second method and the third method in the first embodiment, and there are no significant differences between the obtained composition and the composition obtained by the first method.

What is claimed is:

1. A method for preparing a pharmaceutical composition for enhancing immunity comprising steps of:
   mixing ginseng ethanol extract containing total saponins of *panax ginseng* with fruit and vegetable fermentation conversion solution to obtain a mixture, namely, obtain the pharmaceutical composition for enhancing immunity;
   wherein the ginseng ethanol extract containing total saponins of *panax ginseng* is prepared by a following step of: reflux extracting ginseng by ethanol aqueous solution for obtaining the extract, namely, the ginseng ethanol extract containing total saponins of *panax ginseng*;
   wherein the fruit and vegetable fermentation conversion solution is prepared by following steps of: mixing fruit and vegetable, *lactobacillus acidophilus* bacteria solution, *bifidobacterium longum* bacteria solution, *lactobacillus delbrueckii* subsp. *bulgaricus* bacteria solution, *streptococcus thermophilus* bacteria solution with water, and then fermenting for obtaining a fermentation product, namely, the fruit and vegetable fermentation conversion solution.

2. The method, as recited in claim 1, wherein in the method, every 1 L mixture is prepared by following steps of: mixing the ginseng ethanol extract containing total saponins of *panax* ginseng with the fruit and vegetable fermentation conversion solution, and complementing a volume by the fruit and vegetable fermentation conversion solution for making a concentration of the total saponins of *panax ginseng* in the mixture 1.5 g/l-50 g/l; or every 1 L mixture is prepared by following steps of: mixing the ginseng ethanol extract containing total saponins of *panax ginseng* with the fruit and vegetable fermentation conversion solution, and complementing the volume by the fruit and vegetable fermentation conversion solution for making the concentration of the total saponins of *panax ginseng* in the mixture 1.5 g/l, 15 g/l or 50 g/l.

3. The method, as recited in claim 2, wherein in the method for preparing the ginseng ethanol extract containing total saponins of *panax ginseng*:

a time of every reflux extraction is 2 h-5 h;

a concentration of the ethanol aqueous solution is 70% v/v;

in the method for preparing the fruit and vegetable fermentation conversion solution:

a temperature of the fermentation is 18° C.-37° C., a time of the fermentation is 10 days-180 days, and a mode of the fermentation is fermentation with stirring.

4. The method, as recited in claim 3, wherein the method for preparing the ginseng ethanol extract containing total saponins of *panax ginseng* further comprises following steps of:

removing ethanol from the extract, and then concentrating and drying, thereby obtaining a dried product, namely, the ginseng ethanol extract;

the method for preparing the fruit and vegetable fermentation conversion solution, before fermenting, further comprises a step of grinding the fruit and vegetable with a size of 40-50 meshes;

after fermenting, further comprises steps of: filtering the fermentation product, collecting the filtrate, ultra-filtering, and collecting the ultra-filtered liquid, namely, the fruit and vegetable fermentation conversion solution.

5. The method, as recited in claim 3, wherein the fruit and vegetable is a mixture containing 54 kinds of fruits and vegetables as below:

konjak, eggplant, asparagus, spinach, bean sprouts, cauliflower, cabbage, radish, cucumber, pea, cayenne pepper, celery, green Chinese onion, garlic, grape, grapefruit, watermelon, peach, tangerine, blueberry, sweet orange, banana, litchi, bitter gourd, Chinese chive, pomegranate, pitaya, carrot, tomato, Chinese cabbage, western celery, sweet pepper, lettuce, pear, ginger, taro, kidney bean, pumpkin, lotus root, cherry, kiwi, smoked plum, strawberry, fig, kumquat, citrus, southland pear, muskmelon, melon, papaya, onion, mulberry, sugar beet and lemon.

6. The method, as recited in claim 3, wherein in the fruit and vegetable, every fruit and vegetable has a same weight.

7. The method, as recited in claim 3, wherein in the method for preparing the ginseng ethanol extract containing total saponins of *panax ginseng*:

a ratio of the ethanol aqueous solution to the ginseng is (1-10) ml:1g;

in the method for preparing the fruit and vegetable fermentation conversion solution:

a ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000-8000) ml:(2000-8000) ml:(2000-8000) ml:(2000-8000) ml:(1000-1500) kg:(1000-1500) kg;

the ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg;

the *lactobacillus acidophilus* bacteria solution is prepared by a following step of: fermentally culturing *lactobacillus acidophilus* for obtaining a fermentation product, namely, the *lactobacillus acidophilus* bacteria solution; a fermentation temperature is 20° C.-41° C., a fermentation time is 15 h-36 h;

the *bifidobacterium longum* bacteria solution is prepared by a following step of: fermentally culturing *bifidobacterium longum* for obtaining a fermentation product, namely, the *bifidobacterium longum* bacteria solution; a fermentation temperature is 20° C.-41° C., a fermentation time is 15 h-36 h;

the *lactobacillus delbrueckii* subsp. *bulgaricus* bacteria solution is prepared by a following step of: fermentally culturing *lactobacillus delbrueckii* subsp. *bulgaricus* for obtaining a fermentation product, namely, the *lactobacillus delbrueckii* subsp. *bulgaricus* bacteria solution; a fermentation temperature is 20° C.-41° C., a fermentation time is 15 h-36 h;

the *streptococcus thermophilus* bacteria solution is prepared by a following step of: fermentally culturing *streptococcus thermophilus* for obtaining a fermentation product, namely, the *streptococcus thermophilus* bacteria solution; a fermentation temperature is 20° C.-41° C., a fermentation time is 15 h-36 h.

8. The method, as recited in claim 3, wherein the *lactobacillus acidophilus* is *lactobacillus acidophilus* CGMCC 1.1854, the *bifidobacterium longum* is *bifidobacterium longum* CGMCC 1.2186, the *lactobacillus delbrueckii* subsp. *bulgaricus* is *lactobacillus delbrueckii* subsp. *bulgaricus* CGMCC 1.1480, the *streptococcus thermophilus* is *streptococcus thermophilus* CGMCC 1.2471.

9. A pharmaceutical composition for enhancing immunity prepared by the method recited in claim 3.

10. The method, as recited in claim 2, wherein the method for preparing the ginseng ethanol extract containing total saponins of *panax ginseng* further comprises following steps of:

removing ethanol from the extract, and then concentrating and drying, thereby obtaining a dried product, namely, the ginseng ethanol extract;

the method for preparing the fruit and vegetable fermentation conversion solution, before fermenting, further comprises a step of grinding the fruit and vegetable with a size of 40-50 meshes;

after fermenting, further comprises steps of: filtering the fermentation product, collecting the filtrate, ultra-filtering, and collecting the ultra-filtered liquid, namely, the fruit and vegetable fermentation conversion solution.

11. The method, as recited in claim 2, wherein the fruit and vegetable is a mixture containing 54 kinds of fruits and vegetables as below:

konjak, eggplant, asparagus, spinach, bean sprouts, cauliflower, cabbage, radish, cucumber, pea, cayenne pepper, celery, green Chinese onion, garlic, grape, grapefruit, watermelon, peach, tangerine, blueberry, sweet orange, banana, litchi, bitter gourd, Chinese chive, pomegranate, pitaya, carrot, tomato, Chinese cabbage, western celery, sweet pepper, lettuce, pear, ginger, taro, kidney bean, pumpkin, lotus root, cherry, kiwi, smoked plum, strawberry, fig, kumquat, citrus, southland pear, muskmelon, melon, papaya, onion, mulberry, sugar beet and lemon.

12. The method, as recited in claim 2, wherein in the fruit and vegetable, every fruit and vegetable has a same weight.

13. The method, as recited in claim 2, wherein in the method for preparing the ginseng ethanol extract containing total saponins of *panax ginseng:*
a ratio of the ethanol aqueous solution to the ginseng is (1-10) ml:1g;
in the method for preparing the fruit and vegetable fermentation conversion solution:
a ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000-8000) ml:(2000-8000) ml:(2000-8000) ml:(2000-8000) ml:(1000-1500) kg:(1000-1500) kg;
the ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg;
the *lactobacillus acidophilus* bacteria solution is prepared by a following step of: fermentally culturing *lactobacillus acidophilus* for obtaining a fermentation product, namely, the *lactobacillus acidophilus* bacteria solution; a fermentation temperature is 20° C.-41° C., a fermentation time is 15 h-36 h;
the *bifidobacterium longum* bacteria solution is prepared by a following step of: fermentally culturing *bifidobacterium longum* for obtaining a fermentation product, namely, the *bifidobacterium longum* bacteria solution; a fermentation temperature is 20° C.-41° C., a fermentation time is 15 h-36 h;
the *lactobacillus delbrueckii* subsp. *bulgaricus* bacteria solution is prepared by a following step of: fermentally culturing *lactobacillus delbrueckii* subsp. *bulgaricus* for obtaining a fermentation product, namely, the *lactobacillus delbrueckii* subsp. *bulgaricus* bacteria solution; a fermentation temperature is 20° C.-41° C., a fermentation time is 15 h-36 h;
the *streptococcus thermophilus* bacteria solution is prepared by a following step of: fermentally culturing *streptococcus thermophilus* for obtaining a fermentation product, namely, the *streptococcus thermophilus* bacteria solution; a fermentation temperature is 20° C.-41° C., a fermentation time is 15 h-36 h.

14. The method, as recited in claim 1, wherein in the method for preparing the ginseng ethanol extract containing total saponins of *panax ginseng:*
a time of every reflux extraction is 2 h-5 h;
a concentration of the ethanol aqueous solution is 70% v/v;
in the method for preparing the fruit and vegetable fermentation conversion solution:
a temperature of the fermentation is 18° C.-37° C., a time of the fermentation is 10 days-180 days, and a mode of the fermentation is fermentation with stirring.

15. The method, as recited in claim 14, wherein the method for preparing the ginseng ethanol extract containing total saponins of *panax ginseng* further comprises following steps of:
removing ethanol from the extract, and then concentrating and drying, thereby obtaining a dried product, namely, the ginseng ethanol extract;
the method for preparing the fruit and vegetable fermentation conversion solution,
before fermenting, further comprises a step of grinding the fruit and vegetable with a size of 40-50 meshes;
after fermenting, further comprises steps of: filtering the fermentation product, collecting the filtrate, ultra-filtering, and collecting the ultra-filtered liquid, namely, the fruit and vegetable fermentation conversion solution.

16. The method, as recited in claim 14, wherein the fruit and vegetable is a mixture containing 54 kinds of fruits and vegetables as below:
konjak, eggplant, asparagus, spinach, bean sprouts, cauliflower, cabbage, radish, cucumber, pea, cayenne pepper, celery, green Chinese onion, garlic, grape, grapefruit, watermelon, peach, tangerine, blueberry, sweet orange, banana, litchi, bitter gourd, Chinese chive, pomegranate, pitaya, carrot, tomato, Chinese cabbage, western celery, sweet pepper, lettuce, pear, ginger, taro, kidney bean, pumpkin, lotus root, cherry, kiwi, smoked plum, strawberry, fig, kumquat, citrus, southland pear, muskmelon, melon, papaya, onion, mulberry, sugar beet and lemon.

17. The method, as recited in claim 14, wherein in the fruit and vegetable, every fruit and vegetable has a same weight.

18. The method, as recited in claim 14, wherein in the method for preparing the ginseng ethanol extract containing total saponins of *panax ginseng:*
a ratio of the ethanol aqueous solution to the ginseng is (1-10) ml:1g;
in the method for preparing the fruit and vegetable fermentation conversion solution:
a ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000-8000) ml:(2000-8000) ml:(2000-8000) ml:(2000-8000) ml:(1000-1500) kg:(1000-1500) kg;
the ratio of the *lactobacillus acidophilus* bacteria solution, the *bifidobacterium longum* bacteria solution, the *lactobacillus delbrueckii* subsp. *bulgaricus* bacteria solution, the *streptococcus thermophilus* bacteria solution, the fruit and vegetable and water is (2000, 5000 or 8000) ml:(2000, 5000 or 8000) ml:(2000, 5000 or 8000) ml:(2000, 5000 or 8000) ml:(1000, 1200 or 1500) kg:(1000, 1200 or 1500) kg;
the *lactobacillus acidophilus* bacteria solution is prepared by a following step of: fermentally culturing *lactobacillus acidophilus* for obtaining a fermentation product, namely, the *lactobacillus acidophilus* bacteria solution; a fermentation temperature is 20° C.-41° C., a fermentation time is 15 h-36 h;
the *bifidobacterium longum* bacteria solution is prepared by a following step of: fermentally culturing *bifidobacterium longum* for obtaining a fermentation product, namely, the *bifidobacterium longum* bacteria solution; a fermentation temperature is 20° C.-41° C., a fermentation time is 15 h-36 h;
the *lactobacillus delbrueckii* subsp. *bulgaricus* bacteria solution is prepared by a following step of: fermentally culturing *lactobacillus delbrueckii* subsp. *bulgaricus* for obtaining a fermentation product, namely, the *lactobacillus delbrueckii* subsp. *bulgaricus* bacteria solution; a fermentation temperature is 20° C.-41° C., a fermentation time is 15 h-36 h;

the *streptococcus thermophilus* bacteria solution is prepared by a following step of: fermentally culturing *streptococcus thermophilus* for obtaining a fermentation product, namely, the *streptococcus thermophilus* bacteria solution; a fermentation temperature is 20° C.-41° C., a fermentation time is 15 h-36 h.

19. The method, as recited in claim 14, wherein the *lactobacillus acidophilus* is *lactobacillus acidophilus* CGMCC 1.1854, the *bifidobacterium longum* is *bifidobacterium longum* CGMCC 1.2186, the *lactobacillus delbrueckii* subsp. *bulgaricus* is *lactobacillus delbrueckii* subsp. *bulgaricus* CGMCC 1.1480, the *streptococcus thermophilus* is *streptococcus thermophilus* CGMCC 1.2471.

20. A pharmaceutical composition for enhancing immunity prepared by the method recited in claim 14.

* * * * *